United States Patent [19] [11] 4,183,753

Baigrie et al. [45] Jan. 15, 1980

[54] PHOTOGRAPHIC PRODUCTS AND PROCESSES EMPLOYING METAL COMPLEXED AZO DYES

[75] Inventors: Brian D. Baigrie; Joseph Bailey; Linda G. Johnston; Miroslav V. Mijovic, all of Harrow, England

[73] Assignee: Eastman Kodak Company, Rochester, N.Y.

[21] Appl. No.: 927,189

[22] Filed: Jul. 24, 1978

Related U.S. Application Data

[62] Division of Ser. No. 822,188, Aug. 5, 1977, Pat. No. 4,142,891.

[51] Int. Cl.$^2$ .................... G03C 1/40; C09B 45/00; C09B 45/14; C07C 107/08

[52] U.S. Cl. .................... 430/17; 260/146 R; 260/146 D; 260/146 T; 260/147; 260/149; 260/150; 260/151; 430/223; 430/936; 430/958

[58] Field of Search .................... 96/3, 29 D, 77, 99, 96/84 R, 112; 260/146 R, 146 D, 146 T, 147, 149, 150, 151

[56] References Cited

U.S. PATENT DOCUMENTS

| | | | |
|---|---|---|---|
| 2,868,775 | 1/1959 | Straley et al. | 260/146 R |
| 3,468,871 | 9/1969 | Leverenz et al. | 260/146 R |
| 3,860,571 | 1/1975 | Ramanathan | 260/147 |
| 3,870,695 | 3/1975 | Back et al. | 260/146 R |
| 3,875,139 | 4/1975 | Back et al. | 260/146 R |
| 4,008,211 | 2/1977 | Lienhard et al. | 260/146 R |

*Primary Examiner*—Richard L. Schilling
*Attorney, Agent, or Firm*—Harold E. Cole

[57] ABSTRACT

Photographic elements, diffusion transfer assemblages and processes are described which employ a novel non-diffusible compound having a releasable azo dye moiety such as an arylazo-pyrazolotriazole or arylazo-pyridinol. The compound contains:

(a) a nitrogen atom in a metal chelating location in at least one of the rings attached to the azo group;
(b) in the ortho position of the arylazo moiety a metal chelating group (or a salt thereof or a hydrolyzable precursor thereof), and
(c) a ballasted carrier moiety which is capable of releasing the diffusible azo dye under alkaline conditions.

The dye is transferred imagewise to an image-receiving layer where it is contacted with metal ions to form a metal-complexed azo dye transfer image of excellent stability.

19 Claims, No Drawings

PHOTOGRAPHIC PRODUCTS AND PROCESSES EMPLOYING METAL COMPLEXED AZO DYES

This invention relates to photography and more particularly to color diffusion transfer photography employing certain nondiffusible azo dye-releasing compounds which, as a function of development of a silver halide emulsion layer, release a diffusible, metallizable azo dye. Highly stable metal complexes of this dye are formed in an image-receiving layer.

Azo dye developers containing metallizable groups are disclosed in U.S. Pat. Nos. 3,081,167; 3,196,014; 3,299,041; 3,453,107; and 3,563,739. Since it is a reactive species, however, the developer moiety of such dye developers is capable of developing any exposed silver halide emulsion layer that it comes into contact with, rather than just developing the adjacent silver halide emulsion with which it is associated. Unwanted wrong-layer development, therefore, can occur in dye developer systems which results in undesirable interimage effects. Accordingly, it is desirable to provide an improved transfer system in which the dye is not attached to a "reactive" moiety, such as a developer moiety, so that such dye can diffuse throughout the photographic film unit without becoming immobilized in undesired areas.

In U.S. Published Patent Application B351,673, published Jan. 28, 1975, nondiffusible dye releasing compounds are disclosed. Among the various dye moieties disclosed which can be released are "metal complexed dyes". No specific structures are shown, however.

In U.S. Pat. Nos. 3,931,144; 3,932,380; 3,942,987; 3,954,476; 4,001,209; 4,013,633 and 4,013,635, various nondiffusible azo dye-releasing compounds are disclosed. The released dyes, however, are not disclosed as being metallized or metallizable.

The April 1977 edition of *Research Disclosure,* pages 32 through 39, discloses various nondiffusible dye-releasing compounds and various metallized azo dye fragments. Such premetallized dyes are large molecules which diffuse more slowly than unmetallized dyes, resulting in long access times for image formation. In any event, the specific compounds employed in the instant invention are not disclosed.

U.S. Pat. Nos. 3,086,005; 3,492,287 and 3,985,499 disclose various azo dyes, U.S. Pat. Nos. 2,348,417; 2,495,244; and 2,830,042 and French Pat. Nos. 1,124,882 and 1,200,358 disclose various dyes from azopyridines, while U.S. Pat. Nos. 2,868,775; 2,938,895; 3,097,196; 3,691,161; and 3,875,139; British Pat. No. 899,758; and an article entitled "The Irgalan Dyes—Neutral-Dyeing Metal-Complex Dyes" by Guido Schetty, J. Soc. Dyers and Colourists, Volume 71, 1955, pages 705 through 724, disclose various metal complexed dyes. Again, however, neither the specific compounds employed in the instant invention nor the results obtained therewith are disclosed.

It would be desirable to provide improved dye-releasing compounds containing chelating dye moieties, so that the dye which is released imagewise during processing can diffuse to an image-receiving layer containing metal ions to form a metal-complexed, dye transfer image having better hues, rapid diffusion rates, and shorter access times than those of the prior art, as well as good stability to heat, light and chemical reagents.

A photographic element in accordance with our invention comprises a support having thereon at least one photosensitive silver halide emulsion layer having associated therewith a nondiffusible compound having a releasable azo dye moiety having the following formula:

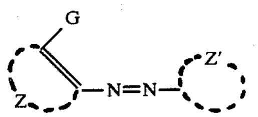

wherein:

Z represents the atoms necessary to complete an aromatic carbocyclic or heterocyclic nucleus having at least one ring of 5 to 7 atoms, such as phenyl, pyridyl, naphthyl, pyrazolyl, indolyl, etc;

Z' is an aromatic carbocyclic or heterocyclic nucleus having at least one ring of 5 to 7 atoms (e.g., the same nuclei as described above for Z), the Z' having, in a position adjacent to the point of attachment to the azo linkage, either (a) a nitrogen atom in the ring of the nucleus which acts as a chelating site, or (b) a carbon atom in the ring of the nucleus having attached thereto a nitrogen atom, either directly or indirectly such as in a sulfamoyl group, which acts as a chelating site;

G is a metal chelating group (any group which will donate a pair of electrons to a metal ion) or a salt thereof (e.g., an alkali metal salt, a quaternary ammonium salt, etc) or a hydrolyzable precursor thereof (e.g., a hydrolyzable acyl or ester group), e.g., hydroxy; amino; carboxy; sulfonamido; sulfamoyl; a hydrolyzable ester group having the formula —$OCOR^1$, —$OCOOR^1$, —$OCON(R^1)_2$ or —$COOR^1$, wherein $R^1$ is an alkyl group having 1 to about 4 carbon atoms, such as methyl, ethyl, isopropyl, butyl and the like, or an aryl group having 6 to about 8 carbon atoms, such as phenyl, etc; or a group which together with

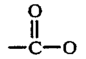

is a ballasted carrier moiety (as defined below) which is attached to the Z-nucleus through the oxygen of the

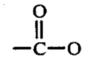

group;

the compound containing a ballasted carrier moiety capable of releasing the diffusible azo dye under alkaline conditions, such as, for example, as a function (either direct or inverse) of development of the silver halide emulsion layer.

In the above formula, G can be either a monovalent group or a nitrogen atom as part of a heterocyclic ring fused to Z. In this later instance, the Z and G atoms can form a nucleus which is the same as the Z' nucleus.

We have found that the use of a nitrogen atom as a chelating site in or adjacent to the ring as described above is generally important in providing metallized dye complexes with narrow spectral absorption bands, much less unwanted absorption, and very good hues. This specific nitrogen atom chelating site is to be contrasted with oxygen atom chelating sites of the hydroxyl and/or carboxyl radicals substituted on aryl nuclei at positions ortho and ortho-prime to the azo linkage, such as described in the above-mentioned U.S. Pat. No. 3,196,014, which generally give rather broad spectra with unwanted absorption.

Z' may be selected from a wide variety of aromatic carbocyclic or heterocyclic nuclei having at least one ring of 5 to 7 atoms and a nitrogen atom in the specific location described above, and include, for example:

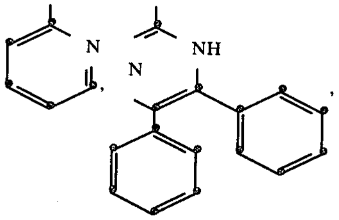

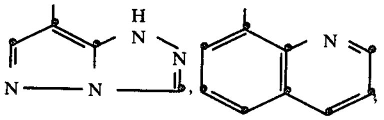

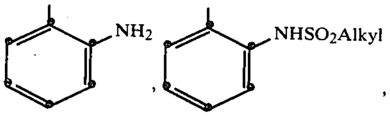

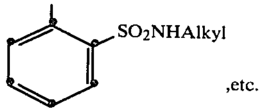

,etc.

wherein "Alkyl" has from 1 to 6 carbon atoms.

In a highly preferred embodiment of our invention, Z represents the atoms necessary to complete an aryl group such as a phenyl group and Z' represents either a pyrazolotriazole nucleus or a pyridinol nucleus. In the former case, the nondiffusible compound may therefore be described as having a releasable arylazo-pyrazolotriazole dye moiety containing:

(a) in the ortho position of the arylazo moiety a metal chelating group, a salt thereof or a hydrolyzable precursor thereof, and (b) a ballasted carrier moiety which is capable of releasing the diffusible arylazo-pyrazolotriazole dye under alkaline conditions, e.g., as a function of development of a silver halide emulsion layer.

In this preferred embodiment of the invention, the arylazo-pyrazolotriazole dye-releasing compound may be represented by the formula:

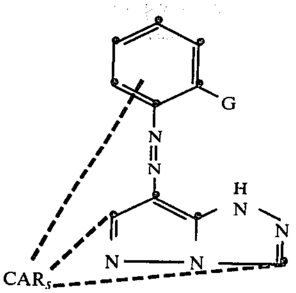

wherein:

G is a metal chelating group, a salt thereof or a hydrolyzable precursor thereof, as defined above, and also includes a group which together with

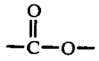

is CAR, the CAR group being attached to the phenyl group through the oxygen of the

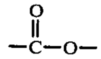

group;

CAR represents the ballasted carrier moiety; and s is a positive integer of 1 to 2, except when G is a group which together with

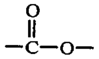

is CAR, in which case s is 0.

It will be appreciated that when s is 2, the compound may be needlessly large and bulky.

In addition to the CAR moiety being attached to the arylazo-pyrazolotriazole dye-releasing compound shown above, the ring structures shown may be substituted with various substituents. For example, if the CAR moiety is attached to the phenyl group, then the alternate position of attachment of CAR to the pyrazole ring can be substituted with alkyl of 1 to 6 carbon atoms, for example, while the triazole ring can be substituted with various substituents such as phenyl, phenyl substituted with alkyl of 1 to 4 carbon atoms, alkoxy, halogens, solubilizing groups such as sulfonamido, sulfamoyl, carboxy, sulfo, hydrolyzable precursors thereof, etc. Similarly, if CAR is attached to the triazole ring, then the phenyl group can be substituted with alkyl of 1 to 4 carbon atoms, alkoxy, halogen, solubilizing groups such as sulfonamido, sulfamoyl, carboxy, sulfo, hydrolyzable precursors thereof, etc, while the pyrazole ring can be substituted in the same manner as described above. If CAR is attached to the pyrazole ring, then the phenyl group and triazole ring can be substituted in the same manner described above. When CAR is attached to one of the positions in the phenyl group, the other positions may be substituted in the manner described above.

In another highly preferred embodiment of the invention, when Z represents an aryl group such as a phenyl group and Z' represents a pyridinol nucleus, the nondiffusible compound may be described as having a releasable 6-arylazo-3-pyridinol dye moiety containing:

(a) in the ortho position of the arylazo moiety a metal chelating group, a salt thereof or a hydrolyzable precursor thereof, and (b) a ballasted carrier moiety which is capable of releasing the diffusible 6-arylazo-3-pyridinol dye under alkaline conditions, e.g., as a function of development of a silver halide emulsion layer.

In this preferred embodiment of the invention, the 6-arylazo-3-pyridinol dye-releasing compound may be represented by the formula:

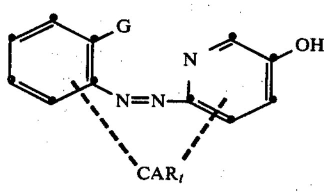

wherein:

G is a metal chelating group, a salt thereof or a hydrolyzable precursor thereof, as defined above;

CAR represents the ballasted carrier moiety; and t is a positive integer of 1 to 2, and preferably is 1.

Good cyan dyes are obtained in this embodiment when the phenyl group is substituted with a nitro group para to the azo linkage, CAR is attached to the pyridine ring, and the pyridine ring is substituted in the 2-position with an amino group, including substituted amino groups such as acylamino, dialkylamino, etc. Other substituents may also be present in the two rings such as alkyl of 1 to 6 carbon atoms, alkoxy, halogens, solubilizing groups such as sulfonamido, sulfamoyl, carboxy, sulfo, hydrolyzable precursors thereof, etc.

When hydrolyzable precursors of the dye moiety of the above compounds are employed, the absorption spectrum of the azo dye is shifted to shorter wavelengths. "Shifted dyes" of this type absorb light outside the range to which the associated silver halide layer is sensitive.

There is great latitude in selecting a CAR moiety which is attached to the azo dye-releasing compounds described above. Depending upon the nature of the ballasted carrier selected, various groups may be needed to attach or link the carrier moiety to the azo dye. Such linking groups are considered to be a part of the CAR moiety in the above definition. It should also be noted that when the dye moiety is released from the compound, cleavage may take place in such a position that part or all of a linking group if one is present, and even part of the ballasted moiety may be transferred to the image-receiving layer along with the dye moiety. In any event, the azo dye nucleus as shown above can be thought of as the "minimum" which is transferred.

CAR moieties useful in the invention are described in U.S. Pat. Nos. 3,227,550; 3,628,952; 3,227,552; and 3,844,785 (dye released by chromogenic coupling); U.S. Pat. Nos. 3,443,939 and 3,443,940 (dye released by intramolecular ring closure); U.S. Pat. Nos. 3,698,897 and 3,725,062 (dye released from hydroquinone derivatives); U.S. Pat. No. 3,728,113 (dye released from a hydroquinonylmethyl quaternary salt); U.S. Pat. Nos. 3,719,489 and 3,443,941 (silver ion induced dye release); and U.S. Pat. Nos. 3,245,789 and 3,980,497; Canadian Pat. No. 602,607; British Pat. No. 1,464,104; *Research Disclosure* 14447, April 1976; and commonly assigned U.S. Application Ser. No. 775,025, filed Mar. 7, 1977, now U.S. Pat. No. 4,139,379, of Chasman et al (dye released by miscellaneous mechanisms), the disclosures of which are hereby incorporated by reference.

In a further preferred embodiment of the invention, the ballasted carrier moiety or CAR as described above may be represented by the following formula:

(Ballast-Carrier-Link)— wherein:

(a) Ballast is an organic ballasting radical of such molecular size and configuration as to render the compound nondiffusible in a photographic element during development in an alkaline processing composition;

(b) Carrier is an oxidizable acyclic, carbocyclic or heterocyclic moiety (see "The Theory of the Photographic Process", by C. E. K. Mees and T. H. James, Third Edition, 1966, pages 282 to 283), e.g., moieties containing atoms according to the following configuration:

$a(-C=C)_b-$ wherein:

b is a positive integer of 1 to 2; and a represents the radicals OH, SH, NH—, or hydrolyzable precursors thereof; and (c) Link represents a group which upon oxidation of said Carrier moiety is capable of being hydrolytically cleaved to release the diffusible azo dye. For example, Link may be the following groups:

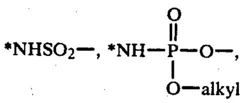

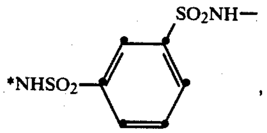

, $*NHSO_2(CH_2)_3NHSO_2-$,

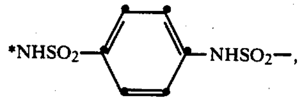

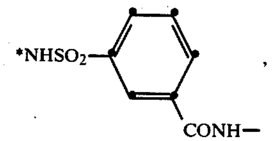

,

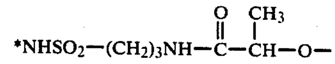

wherein * represents the position of attachment to Carrier.

The Ballast group in the above formula is not critical as long as it confers nondiffusibility to the compound. Typical Ballast groups include long-chain alkyl radicals linked directly or indirectly to the compound as well as aromatic radicals of the benzene and naphthalene series indirectly attached or fused directly to the carbocyclic or heterocyclic nucleus, etc. Useful Ballast groups generally have at least 8 carbon atoms such as substituted or unsubstituted alkyl groups of 8 to 22 carbon atoms, a carbamoyl radical having 8 to 30 carbon atoms such as $-CONH(CH_2)_4-O-C_6H_3(C_5H_{11})_2$, $-CON(C_{12}H_{25})_2$, etc, a keto radical having 8 to 30 carbon atoms such as $-CO-C_{17}H_{35}$, $-CO-C_6H_4-(t-C_{12}H_{25})$, etc.

For specific examples of Ballast-Carrier-Link moieties useful as the CAR moiety in this invention, reference is made to the November 1976 edition of *Research Disclosure,* pages 68 through 74, and the April 1977 edition of *Research Disclosure,* pages 32 through 39, the disclosures of which are hereby incorporated by reference.

In a highly preferred embodiment of the invention, the ballasted carrier moiety or CAR in the above formulas is a group having the formula:

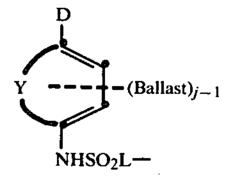

wherein:

(a) Ballast is an organic ballasting radical of such molecular size and configuration (e.g., simple organic groups or polymeric groups) as to render the compound nondiffusible in a photographic element during development in an alkaline processing composition;

(b) D is $OR^2$ or $NHR^3$ wherein $R^2$ is hydrogen or a hydrolyzable moiety and $R^3$ is hydrogen or a substituted or unsubstituted alkyl group of 1 to 22 carbon atoms such as methyl, ethyl, hydroxyethyl, propyl, butyl, secondary butyl, tert-butyl, cyclopropyl, 4-chlorobutyl, cyclobutyl, 4-nitroamyl, hexyl, cyclohexyl, octyl, decyl, octadecyl, dodecyl, benzyl, phenethyl, etc. (when $R^3$ is an alkyl group of greater than 8 carbon atoms, it can serve as a partial or sole Ballast);

(c) Y represents the atoms necessary to complete a benzene nucleus, a naphthalene nucleus, or a 5 to 7 membered heterocyclic ring such as pyrazolone, pyrimidine, etc;

(d) j is a positive integer of 1 to 2 and is 2 when D is $OR^2$ or when $R^3$ is hydrogen or an alkyl group of less than 8 carbon atoms; and (e) L is a linking group which is $[X-(NR^4-J)_q]_m-$ or $X-J-NR^4-$ wherein:

(i) X represents a bivalent linking group of the formula $-R^5-L'_n-R^5_p-$ where each $R^5$ can be the same or different and each represents an alkylene radical having 1 to about 8 carbon atoms, such as methylene, hexylene and the like; a phenylene radical; or a substituted phenylene radical having 6 to about 9 carbon atoms, such as methoxy phenylene;

(ii) L' represents a bivalent radical selected from oxy, carbonyl, carboxamido, carbamoyl, sulfonamido, ureylene, sulfamoyl, sulfinyl or sulfonyl;

(iii) n is an integer of 0 or 1;

(iv) p is 1 when n equals 1 and p is 1 or 0 when n equals 0, provided that when p is 1 the carbon content of the sum of both $R^5$ radicals does not exceed 14 carbon atoms;

(v) $R^4$ represents a hydrogen atom, or an alkyl radical having 1 to about 6 carbon atoms;

(vi) J represents a bivalent radical selected from sulfonyl or carbonyl;

(vii) q represents an integer of 0 or 1; and (viii) m represents an integer of 0, 1 or 2.

Especially good results are obtained in the above formula when D is OH, j is 2, Y is a naphthalene nucleus, and G is OH.

Examples of the CAR moiety in this highly preferred embodiment are disclosed in U.S. Published Patent Application B351,673; U.S. Pat. No. 3,928,312; French Pat. No. 2,284,140; and German Pat. Nos. 2,406,664; 2,613,005; and 2,505,248, the disclosures of which are hereby incorporated by reference, and include the following:

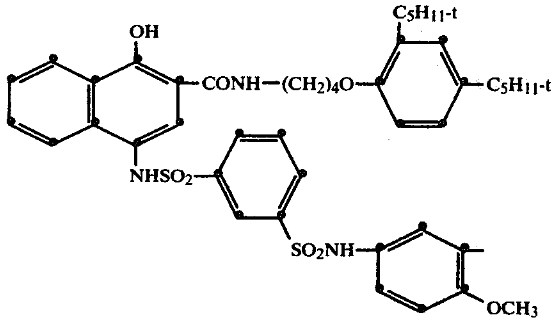

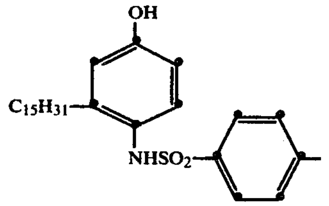

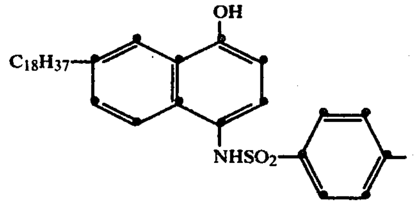

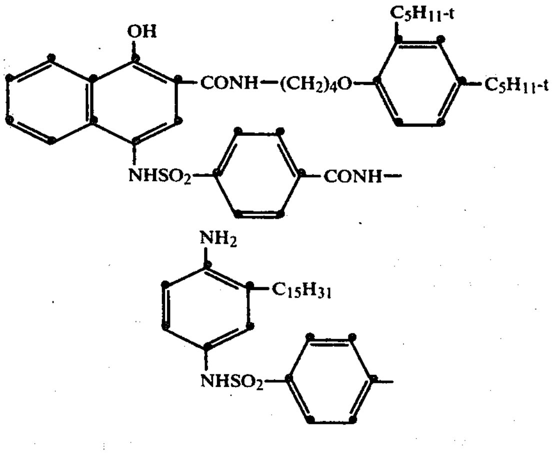

In another highly preferred embodiment of the invention, the ballasted carrier moiety or CAR in the above formulas is such that the diffusible azo dye is released as an inverse function of development of the silver halide emulsion layer under alkaline conditions. This is ordinarily referred to as positive-working dye-release chemistry. In one of these embodiments, the ballasted carrier moiety or CAR in the above formulas may be a group having the formula:

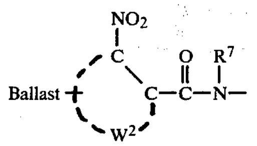

(I)

wherein:

Ballast is an organic ballasting radical of such molecular size and configuration as to render the compound nondiffusible in a photographic element during development in an alkaline processing composition;

$W^2$ represents at least the atoms necessary to complete a benzene nucleus (including various substituents thereon); and $R^7$ is an alkyl (including substituted alkyl) radical having 1 to about 4 carbon atoms.

Examples of the CAR moiety in this formula I include the following:

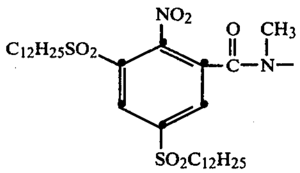

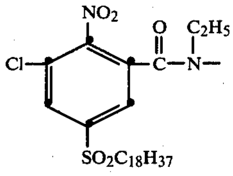

In a second embodiment of positive-working dye-release chemistry as referred to above, the ballasted carrier moiety or CAR in the above formulas may be a group having the formula:

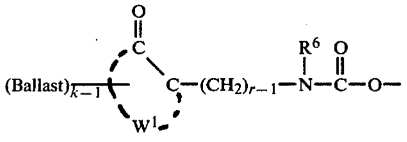

(II)

wherein:

Ballast is an organic ballasting radical of such molecular size and configuration as to render the compound nondiffusible in a photographic element during development in an alkaline processing composition;

$W^1$ represents at least the atoms necessary to complete a quinone nucleus (including various substituents thereon);

r is a positive integer of 1 or 2;

$R^6$ is an alkyl (including substituted alkyl) radical having 1 to about 40 carbon atoms or an aryl (including substituted aryl) radical having 6 to about 40 carbon atoms; and k is a positive integer of 1 to 2 and is 2 when $R^6$ is a radical of less than 8 carbon atoms.

Examples of the CAR moiety in this formula II include the following:

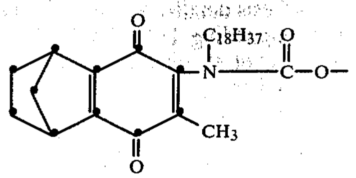

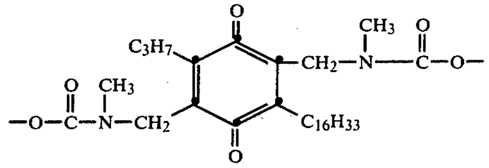

In using the compounds in formulas I and II above, they are employed in a photographic element similar to the other nondiffusible dye-releasers described previously. Upon reduction of the compound as a function of silver halide development under alkaline conditions, the metallizable azo dye is released. In this embodiment, conventional negative-working silver halide emulsions, as well as direct-positive emulsions, can be employed. For further details concerning these particular CAR moieties, including synthesis details, reference is made to commonly assigned copending U.S. Application Ser. No. 775,025 of Chasman et al, filed Mar. 7, 1977, the disclosure of which is hereby incorporated by reference.

In a third embodiment of positive-working dye-release chemistry as referred to above, the ballasted carrier moiety or CAR in the above formulas may be a group having the formula:

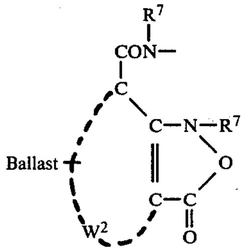

(III)

wherein:

Ballast, $W^2$ and $R^7$ are as defined for formula I above.

Examples of the CAR moiety in this formula III include the following:

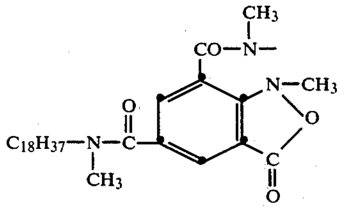

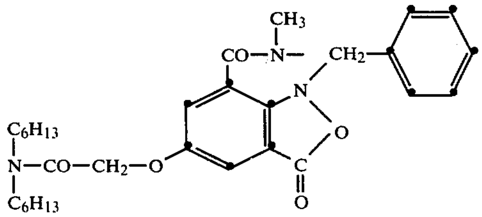

For further details concerning this particular CAR moiety, including synthesis details, reference is made to commonly assigned copending U.S. Application Ser. No. 534,966 of Hinshaw et al, filed Dec. 20, 1974, the disclosure of which is hereby incorporated by reference.

In a fourth embodiment of positive-working dye-release chemistry as referred to above, the ballasted carrier moiety or CAR in the above formulas may be a group having the formula:

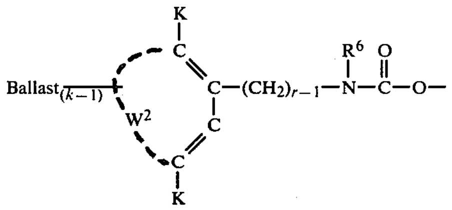

(IV)

wherein:

Ballast, r, $R^6$ and k are as defined for formula II above;

$W^2$ is as defined for formula I above; and

K is OH or a hydrolyzable precursor thereof.

Examples of the CAR moiety in this formula IV include the following:

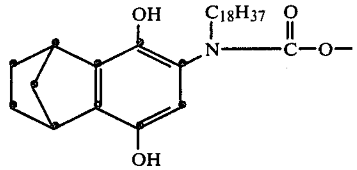

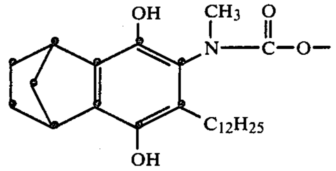

For further details concerning this particular CAR moiety, including synthesis details, reference is made to U.S. Pat. No. 3,980,479 of Fields et al, issued Sept. 14, 1976, the disclosure of which is hereby incorporated by reference.

Representative compounds included within the scope of the invention include the following:

(1)

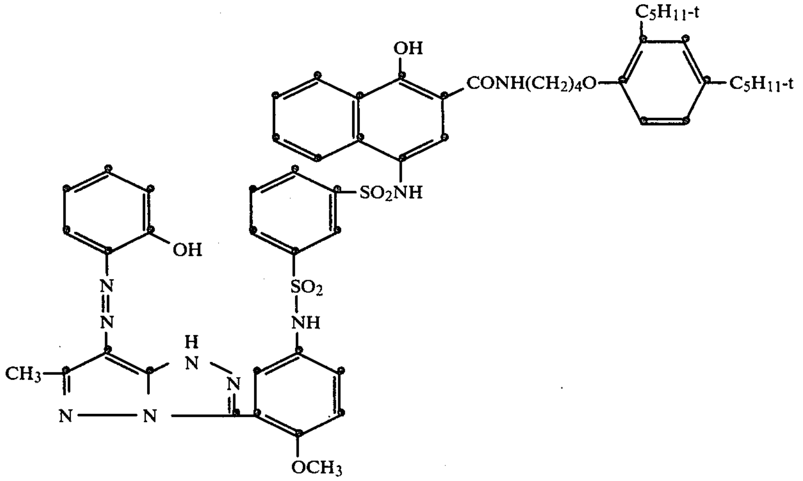

(2)

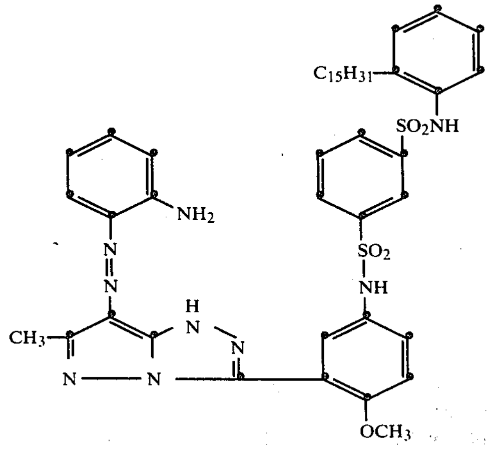

-continued
(3)
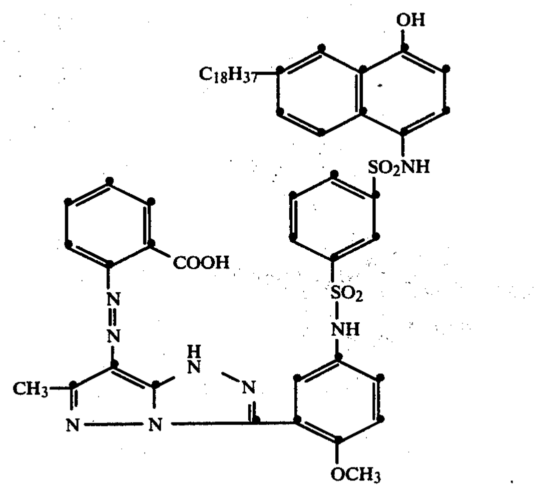
(4)
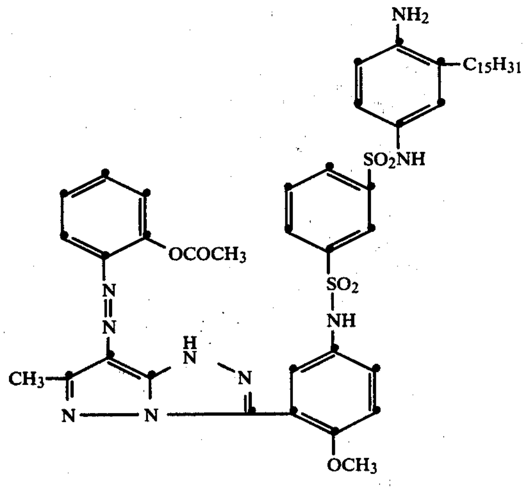
(5)
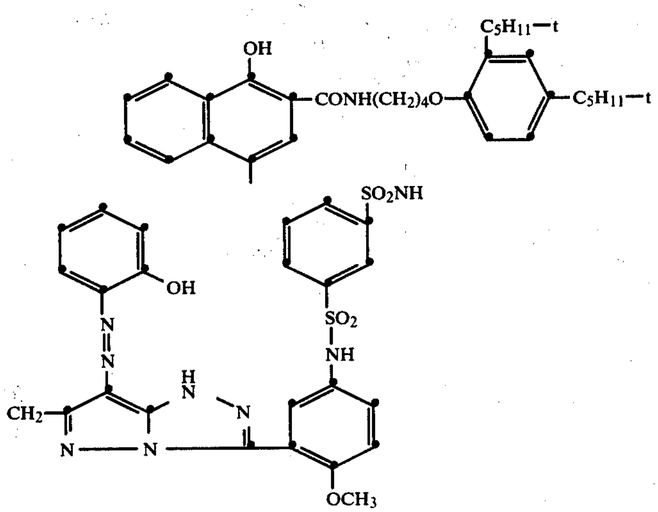

-continued
(6)
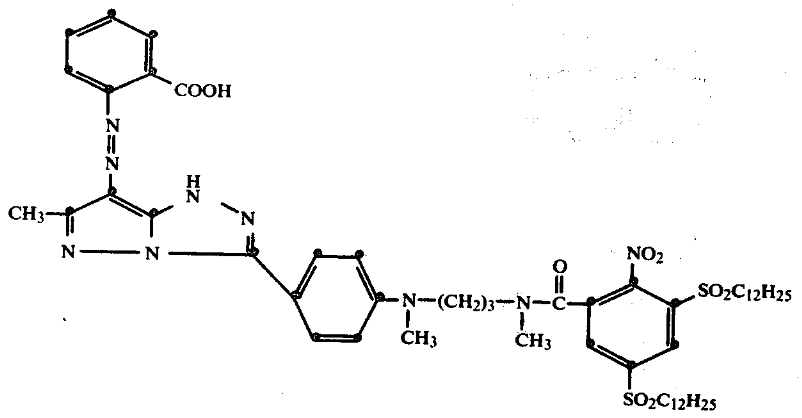
(7)
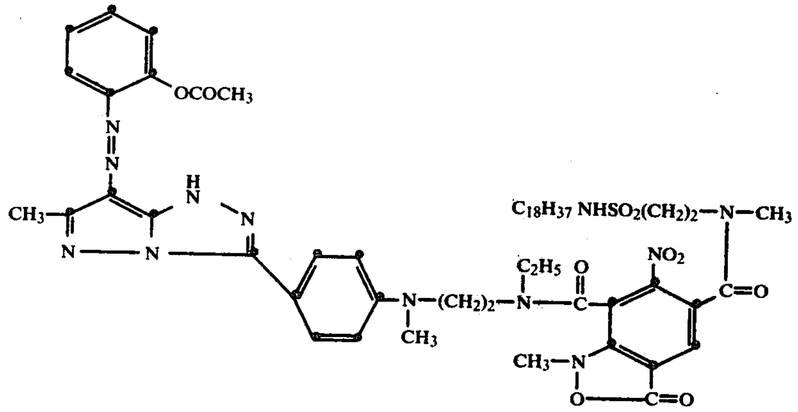
(8)
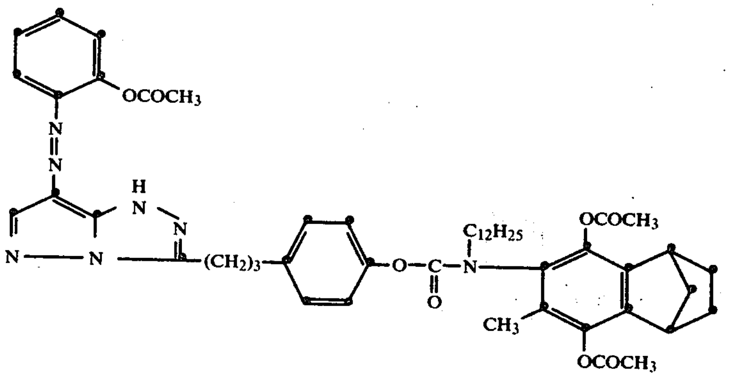
(9)
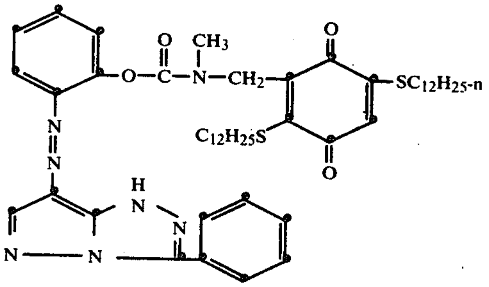

-continued
(10)
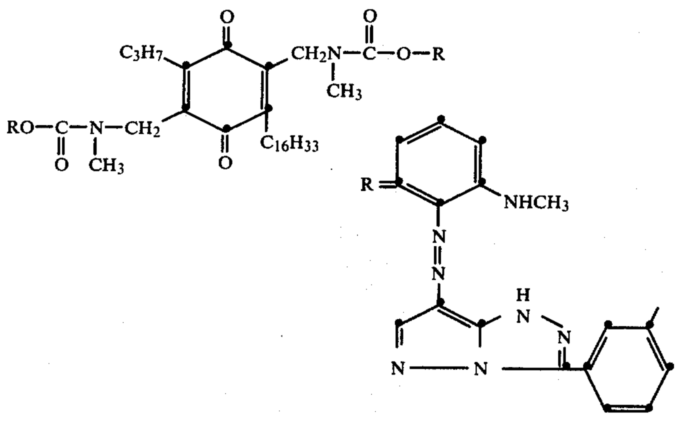
(11)
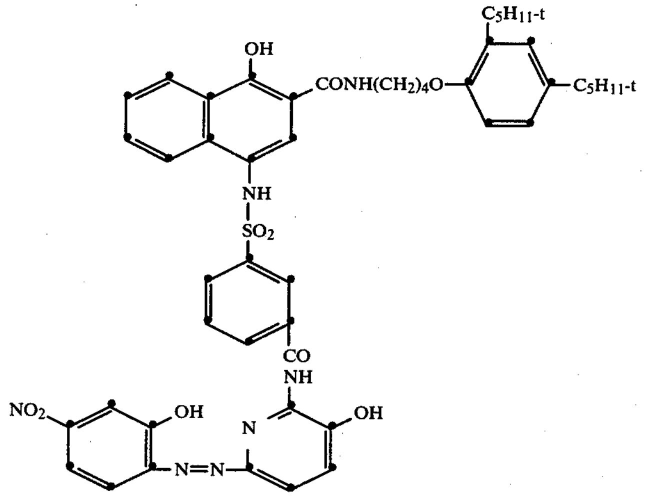
(12)
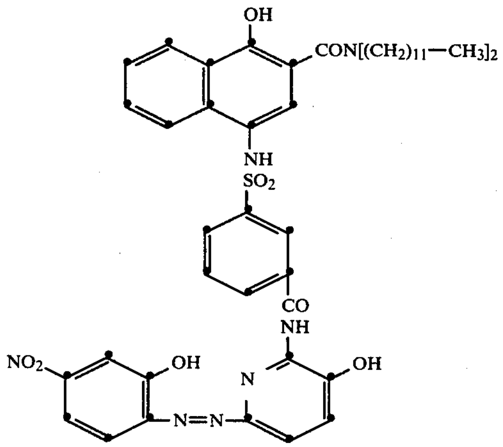

-continued
(13)
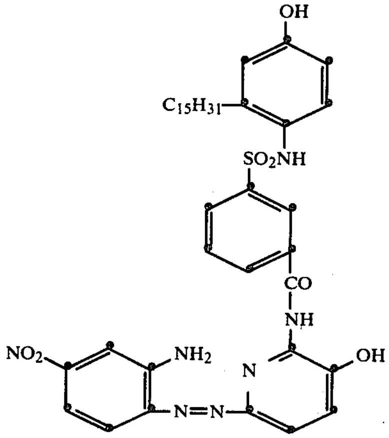
(14)
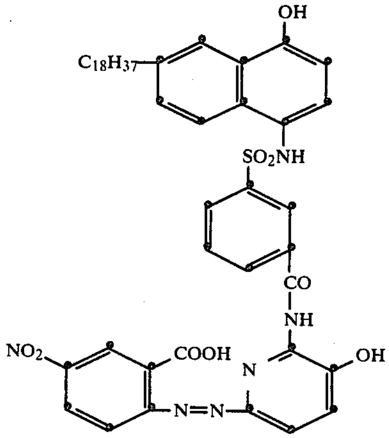
(15)
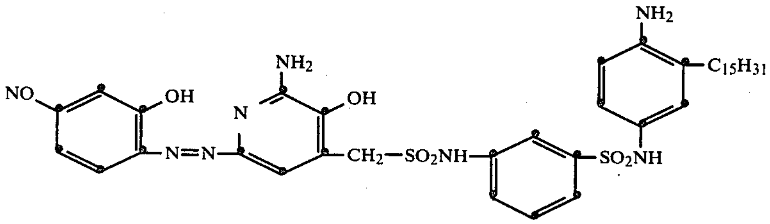
(16)
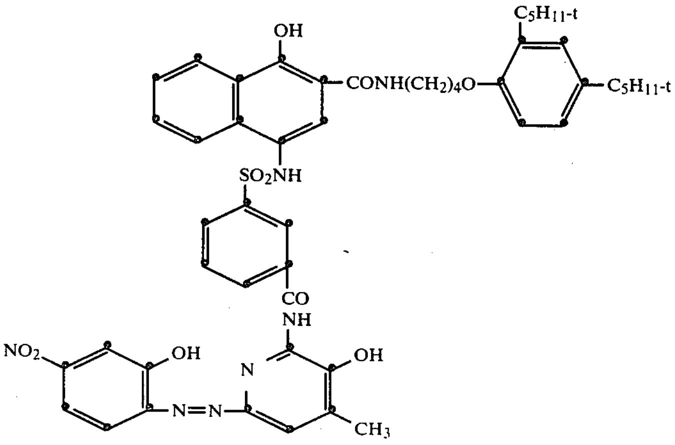

-continued
(17)
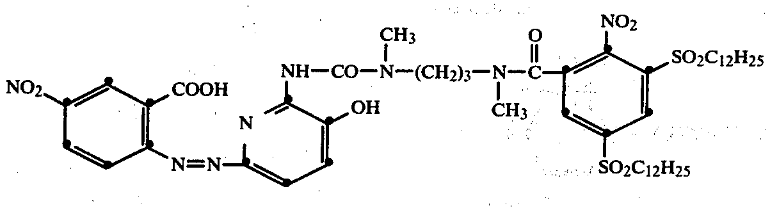
(18)
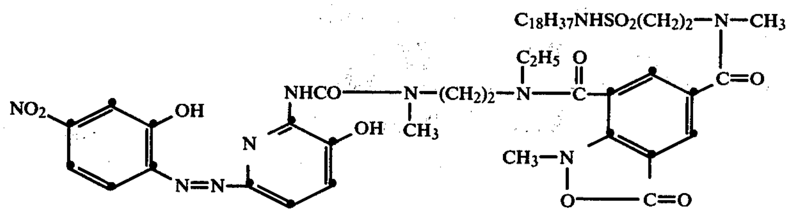
(19)
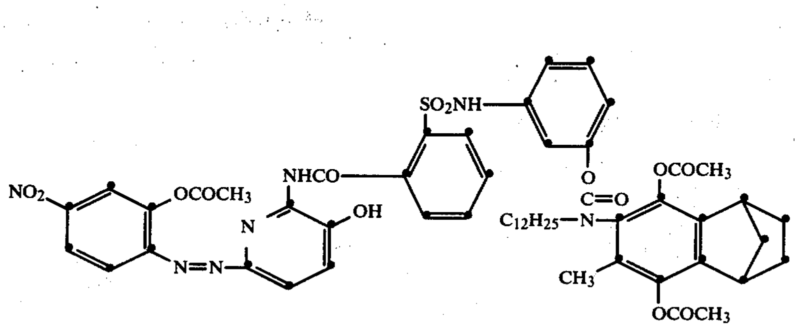
(20)
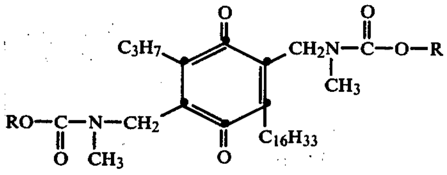
R =
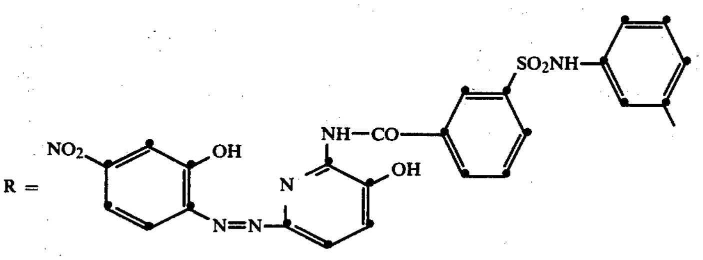
(21)
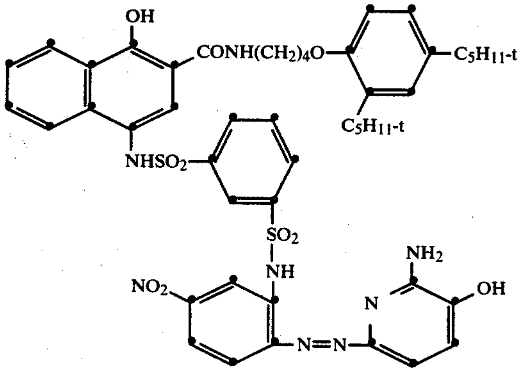

-continued
(22)
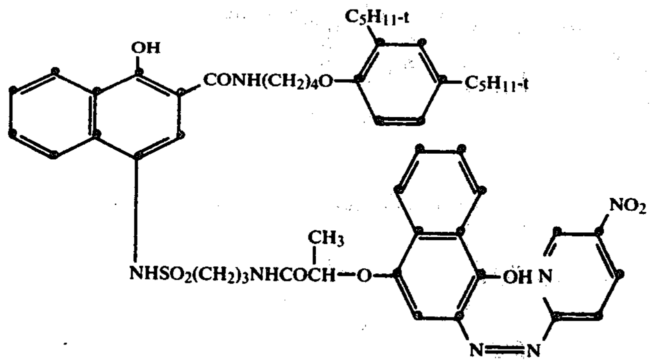
(23)
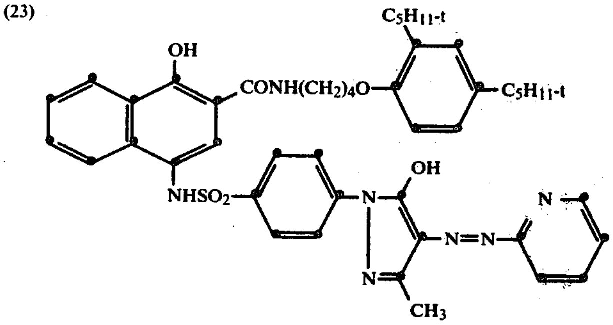
(24)
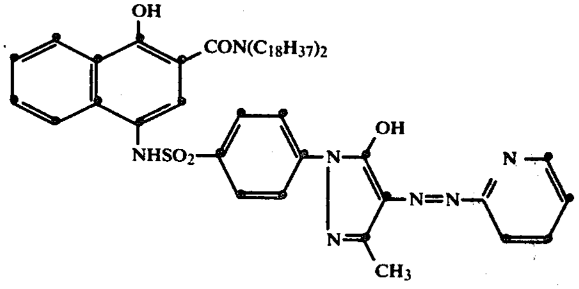
(25)
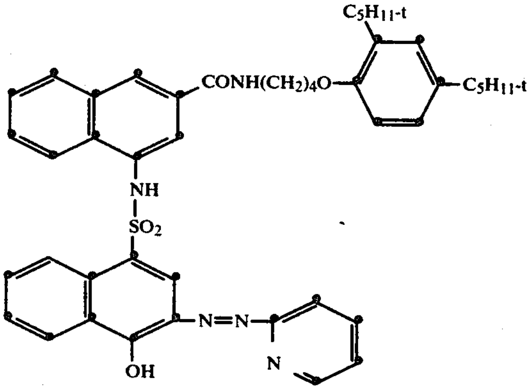

-continued (26)

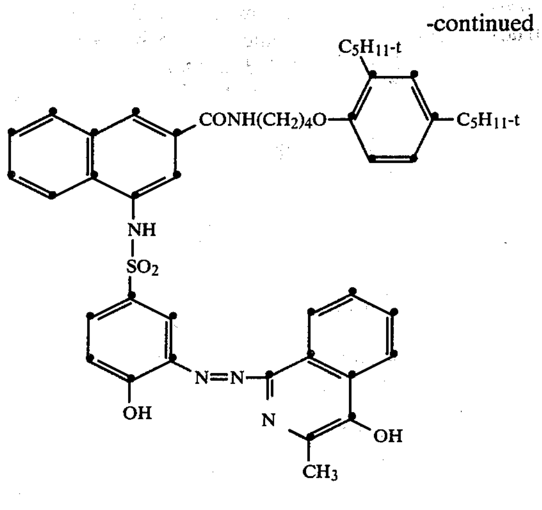

Compound 21 is the subject of an invention by our coworker, Derek D. Chapman, in copending U.S. Application Ser. No. 822,189, filed Aug. 5, 1977, commonly assigned to Eastman Kodak Company. Compound 22 is the subject of an invention by our coworkers Richard B. Anderson, Elaine H. Hoffmeister and Richard A. Landholm, in copending U.S. Application Ser. No. 832,499, filed Sept. 12, 1977, commonly assigned to Eastman Kodak Company. Compounds 23 and 24 are the subject of an invention by our coworkers, James A. Green and Norman W. Kalenda, in copending U.S. Application Ser. No. 832,310, filed Sept. 12, 1977, commonly assigned to Eastman Kodak Company. Compound 25 is the subject of an invention by our coworkers, Derek D. Chapman and E-Ming Wu, in copending U.S. Application Ser. No. 832,309, filed Sept. 12, 1977, commonly assigned to Eastman Kodak Company. Compound 26 is the subject of an invention by our coworkers Derek D. Chapman, James A. Friday, and James K. Elwood, in copending U.S. Application Ser. No. 884,469, filed Mar. 7, 1978, commonly assigned to Eastman Kodak Company.

A process for producing a photographic transfer image in color according to our invention comprises:

(a) treating an imagewise-exposed photographic element as described above with an alkaline processing composition in the presence of a silver halide developing agent to effect development of each of the exposed silver halide emulsion layers, (b) the dye-releasing compound then releasing the diffusible azo dye as described above imagewise as a function of the development of each of the silver halide emulsion layers;

(c) at least a portion of the imagewise distribution of the azo dye diffusing to a dye image-receiving layer; and (d) contacting the imagewise distribution of azo dye with metal ions, thereby forming a metal-complexed azo dye transfer image.

In another preferred embodiment of our invention, a process for producing a photographic transfer image in color according to our invention comprises:

(a) treating an imagewise-exposed photographic element as described above wherein CAR in the compound has the formula:

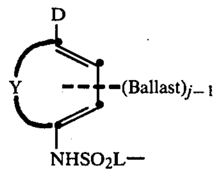

D, Y, L and j being defined as above, with an alkaline processing composition in the presence of a silver halide developing agent to effect development of each of the exposed silver halide emulsion layers, thereby oxidizing the development agent;

(b) the oxidized developing agent thereby cross-oxidizing the dye-releasing compound;

(c) the cross-oxidized dye-releasing compound then cleaving as a result of alkaline hydrolysis to release the diffusible azo dye imagewise as a function of the imagewise exposure of each of the silver halide emulsion layers;

(d) at least a portion of the imagewise distribution of the azo dye diffusing to a dye image-receiving layer; and (e) contacting the imagewise distribution of azo dye with metal ions, thereby forming a metal-complexed azo dye transfer image.

The tridentate azo dye ligand which is released form the dye-releasing compounds in accordance with the present invention will form a coordination complex in the image-receiving layer with polyvalent metal ions. The metal ions can be present in the image-receiving layer itself or in a layer adjacent thereto, or the image-receiving layer can be contacted with metal ions in a bath after diffusion of the dye has taken place. Metal ions most useful in the invention are those which: are essentially colorless when incorporated into the image-receiving element, are inert with respect to the silver halide layers, react readily with the released dye to form a complex of the desired hue, are tightly coordinated to the dye in the complex, have a stable oxidation state, and form a dye complex which is stable to heat, light and chemical reagents. In general, good results are obtained with polyvalent metal ions such as copper (II), zinc (II), nickel (II), platinum (II), palladium (II) and cobalt (II) ions.

For example, it is believed that the coordination complexes which are formed from the tridentate azo dye ligands according to the invention in two of the preferred embodiments thereof have the following structures:

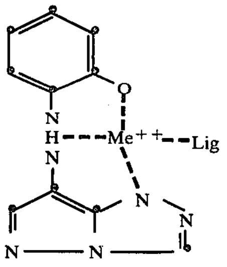

and

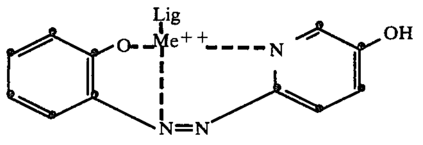

where Me is metal and Lig is one or more ligand groups depending upon the coordination number of the metal ion, such as $H_2O$, Cl, pyridine, etc.

Thus, in accordance with another embodiment of our invention, a photographic element is provided which comprises a support having thereon a coordination complex of a polyvalent metal ion and a compound having the formula:

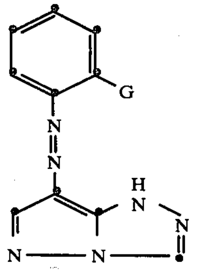

or

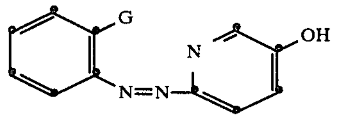

wherein G is a metal chelating group, e.g., those as described previously. The element usually contains a photographic mordant or image-receiving layer to bind the dye or coordination complex thereto. The structures shown above may also, of course, be substituted in the same manner as described above for the starting compounds from which they are released, e.g., in the pyridinol compound, the phenyl group may have a nitro group para to the azo linkage and an amino group present in the 2-position in the pyridine ring, etc.

It will be appreciated that, after processing the photographic element described above, there remains in it, after transfer has taken place, an imagewise distribution of azo dye in addition to developed silver. A color image comprising residual nondiffusible compound may be obtained in this element if the residual silver and silver halide are removed by any conventional manner well known to those skilled in the photographic art, such as a bleach bath followed by a fix bath, a bleach-fix bath, etc. Such a retained dye image should normally be treated with metal ions to metallize the dyes to increase their light fastness and shift their spectral absorption to the intended region. The imagewise distribution of azo dye may also diffuse out of the element into these baths, if desired, rather than to an image-receiving element. If a negative-working silver halide emulsion is employed in certain preferred photosensitive elements, described above, then a positive color image, such as a reflection print, a color transparency or a motion picture film, may be produced in this manner. If a direct-positive silver halide emulsion is employed in such photosensitive elements, then a negative color image may be produced.

The photographic element in the above-described process can be treated with an alkaline processing composition to effect or initiate development in any manner. A preferred method for applying processing composition is by use of a rupturable container or pod which contains the composition. In general, the processing composition employed in this invention contains the developing agent for development, although the composition could also just be an alkaline solution where the developer is incorporated in the photographic element, the image-receiving element or the process sheet, in which case the alkaline solution serves to activate the incorporated developer.

A photographic film unit which can be processed in accordance with this invention is adapted to be processed by passing the unit between a pair of juxtaposed pressure-applying members, such as would be found in a camera designed for incamera processing, and comprises:

(1) a photographic element as described above;

(2) a dye image-receiving layer; and (3) means for discharging an alkaline processing composition within the film unit, such as a rupturable container which is adapted to be positioned during processing of the film unit so that a compressive force applied to the container by the pressure-applying members will effect a discharge of the container's contents within the film unit;

the film unit containing a silver halide developing agent.

In the embodiment described above, the dye image-receiving layer may itself contain metal ions, or the metal ions may be present in an adjacent layer, so that the tridentate azo dye ligand which is released will form a coordination complex therewith. The dye thus becomes immobilized in the dye image-receiving layer and metallized at the same time. Alternatively, the dye image in the dye image-receiving layer may be treated with a solution containing metal ions to effect metallization. The formation of the coordination complex shifts the absorption of the dye to the desired hue, usually to longer wavelengths, which have a different absorption than that of the initial dye-releasing compound. If this shift is large enough, then the dye-releasing compound may be incorporated in a silver halide emulsion layer without adversely affecting its sensitivity.

The dye image-receiving layer in the above-described film unit can be located on a separate support adapted to be superposed on the photographic element after exposure thereof. Such image-receiving elements are generally disclosed, for example, in U.S. Pat. No. 3,362,819. When the means for discharging the processing composition in a rupturable container, it is usually positioned in relation to the photographic element and the image-receiving element so that a compressive force applied to the container by pressure-applying members, such as would be found in a typical camera used for in-camera processing, will effect a discharge of the container's contents between the image-receiving element and the outermost layer of the photographic element. After processing, the dye image-receiving element is separated from the photographic element.

The dye image-receiving layer in the above-described film unit can also be located integral with the photographic element between the support and the lowermost photosensitive silver halide emulsion layer. One useful format for integral receiver-negative photographic elements is disclosed in Belgian Pat. No. 757,960. In such an embodiment, the support for the photographic element is transparent and is coated with an image-receiving layer, a substantially opaque light-reflective layer, e.g., $TiO_2$, and then the photosensitive layer or layers described above. After exposure of the photographic element, a rupturable container containing an alkaline processing composition and an opaque process sheet are brought into superposed position. Pressure-applying members in the camera rupture the container and spread processing composition over the photographic element as the film unit is withdrawn from the camera. The processing composition develops each exposed silver halide emulsion layer, and dye images, formed as a function of development, diffuse to the image-receiving layer to provide a positive, right-reading image which is viewed through the transparent support on the opaque reflecting layer background. For other details concerning the format of this particular integral film unit, reference is made to the above-mentioned Belgian Pat. No. 757,960.

Another format for integral negative-receiver photographic elements in which the present invention can be employed is disclosed in Belgian Pat. No. 757,959. In this embodiment, the support for the photographic element is transparent and is coated with the image-receiving layer, a substantially opaque, light-reflective layer and the photosensitive layer or layers described above. A rupturable container containing an alkaline processing composition and an opacifier is positioned adjacent the top layer and a transparent top sheet which has thereon a neutralizing layer and a timing layer. The film unit is placed in a camera, exposed through the transparent top sheet and then passed through a pair of pressure-applying members in the camera as it is being removed therefrom. The pressure-applying members rupture the container and spread processing composition and opacifier over the negative portion of the film unit to render it light-insensitive. The processing composition develops each silver halide layer and dye images, formed as a result of development, diffuse to the image-receiving layer to provide a positive, right-reading image which is viewed through the transparent support on the opaque reflecting layer background. For further details concerning the format of this particular integral film unit, reference is made to the above-mentioned Belgian Pat. No. 757,959.

Still other useful integral formats in which this invention can be employed are described in U.S. Pat. Nos. 3,415,644; 3,415,645; 3,415,646; 3,647,437; and 3,635,707. In most of these formats, a photosensitive silver halide emulsion is coated on an opaque support, and a dye image-receiving layer is located on a separate transparent support superposed over the layer outermost from the opaque support. In addition, this transparent support also preferably contains a neutralizing layer and a timing layer underneath the dye image-receiving layer.

Another embodiment of the invention uses the image-reversing technique disclosed in British Pat. No. 904,364, page 19, lines 1 through 41. In this process, the dye-releasing compounds are used in combination with physical development nuclei in a nuclei layer contiguous to the photosensitive silver halide negative emulsion layer. The film unit contains a silver halide solvent, preferably in a rupturable container with the alkaline processing composition.

The film unit or assembly used in the present invention may be used to produce positive images in single- or multicolors. In a three-color system, each silver halide emulsion layer of the film assembly will have associated therewith a dye-releasing compound which releases a dye possessing a predominant spectral absorption within the region of the visible spectrum to which said silver halide emulsion is sensitive (initially or after forming the coordination complex), i.e., the blue-sensitive silver halide emulsion layer will have a yellow or yellow-forming dye-releaser associated therewith, the green-sensitive silver halide emulsion layer will have a magenta or magenta-forming dye-releaser associated therewith, and the red-sensitive silver halide emulsion layer will have a cyan or cyan-forming dye-releaser associated therewith, at least one of the dye-releasers being a compound in accordance with the present invention. The dye-releaser associated with each silver halide emulsion layer may be contained either in the silver halide emulsion layer itself or in a layer contiguous to the slver halide emulsion layer.

The concentration of the dye-releasing compounds that are employed in the present invention may be varied over a wide range, depending upon the particular compound employed and the results desired. For example, the dye-releasers of the present invention may be coated in layers by using coating solutions containing between about 0.5 and about 8 percent by weight of the dye-releaser distributed in a hydrophilic film-forming natural material or synthetic polymer, such as gelatin, polyvinyl alcohol, etc, which is adapted to be permeated by aqueous alkaline processing composition.

Depending upon which CAR is used in the present invention, a variety of silver halide developing agents can be employed. In certain embodiments of the invention, any silver halide developing agent can be employed as long as it cross-oxidizes with the dye-releasers described herein. The developer may be employed in the photosensitive element to be activated by the alkaline processing composition. Specific examples of developers which can be employed in this invention include:

N-methylaminophenol
Phenidone (1-phenyl-3-pyrazolidone)
Dimezone (1-phenyl-4,4-dimethyl-3-pyrazolidone)
aminophenols
1-phenyl-4-methyl-4-hydroxymethyl-3-pyrazolidone
N,N-diethyl-p-phenylenediamine
N,N,N',N'-tetramethyl-p-phenylenediamine
3-methyl-N,N-diethyl-p-phenylenediamine
3-methoxy-N-ethyl-N-ethoxy-p-phenylenediamine, etc.

The non-chromogenic developers in this list are preferred, however, since they avoid any propensity of staining the dye image-receiving layer.

In one of the preferred embodiments of the invention, the silver halide developer employed in the process becomes oxidized upon development and reduces silver halide to silver metal. The oxidized developer then cross-oxidizes the dye-releasing compound. The product of cross-oxidation then undergoes alkaline hydrolysis, thus releasing an imagewise distribution of diffusible azo dye which then diffuses to the receiving layer to provide the dye image. The diffusible moiety is transferable in alkaline processing composition either by virtue of its self-diffusivity or by its having attached to it one or more solubilizing groups, for example, a carboxy, sulpho, sulphonamido, hydroxy or morpholino group.

In using the dye-releasing compounds according to the invention which produce diffusible dye images as a function of development, either conventional negative-working or direct-positive silver halide emulsions may be employed. If the silver halide emulsion employed is a direct-positive silver halide emulsion, such as an internal-image emulsion designed for use in the internal image reversal process, or a fogged, direct-positive emulsion such as a solarizing emulsion, which is developable in unexposed areas, a positive image can be obtained in certain embodiments on the dye image-receiving layer. After exposure of the film unit, the alkaline processing composition permeates the various layers to initiate development of the exposed photosensitive silver halide emulsion layers. The developing agent present in the film unit develops each of the silver halide emulsion layers in the unexposed areas (since the silver halide emulsions are direct-positive ones), thus causing the developing agent to become oxidized imagewise corresponding to the unexposed areas of the direct-positive silver halide emulsion layers. The oxidized developing agent then cross-oxidizes the dye-releasing compounds and the oxidized form of the compounds then undergoes a base-catalyzed reaction to release the dyes imagewise as a function of the imagewise exposure of each of the silver halide emulsion layers. At least a portion of the imagewise distributions of diffusible dyes diffuse to the image-receiving layer to form a positive image of the original subject. After being contacted by the alkaline processing composition, a pH-lowering layer in the film unit or image-receiving unit lowers the pH of the film unit or image receiver to stabilize the image.

Internal-image silver halide emulsions useful in this invention are described more fully in the November 1976 edition of *Research Disclosure,* pages 76 through 79, the disclosure of which is hereby incorporated by reference.

The various silver halide emulsion layers of a color film assembly employed in this invention can be disposed in the usual order, i.e., the blue-sensitive silver halide emulsion layer first with respect to the exposure side, followed by the green-sensitive and red-sensitive silver halide emulsion layers. If desired, a yellow dye layer or a yellow colloidal silver layer can be present between the blue-sensitive and green-sensitive silver halide emulsion layers for absorbing or filtering blue radiation that may be transmitted through the blue-sensitive layer. If desired, the selectively sensitized silver halide emulsion layers can be disposed in a different order, e.g., the blue-sensitive layer first with respect to the exposure side, followed by the red-sensitive and green-sensitive layers.

The rupturable container employed in certain embodiments of this invention can be of the type disclosed in U.S. Pat. Nos. 2,543,181; 2,643,886; 2,653,732; 2,723,051; 3,056,492; 3,056,491 and 3,152,515. In general, such containers comprise a rectangular sheet of fluid- and air-impervious material folded longitudinally upon itself to form two walls which are sealed to one another along their longitudinal and end margins to form a cavity in which processing solution is contained.

Generally speaking, except where noted otherwise, the silver halide emulsion layers employed in the invention comprise photosensitive silver halide dispersed in gelatin and are about 0.6 to 6 microns in thickness; the dye-releasers are dispersed in an aqueous alkaline solution-permeable polymeric binder, such as gelatin, as a separate layer about 0.2 to 7 microns in thickness; and the alkaline solution-permeable polymeric interlayers, e.g., gelatin, are about 0.2 to 5 microns in thickness. Of course, these thicknesses are approximate only and can be modified according to the product desired.

Scavengers for oxidized developing agent can be employed in various interlayers of the photographic elements of the invention. Suitable materials are disclosed on page 83 of the November 1976 edition of *Research Disclosure,* the disclosure of which is hereby incorporated by reference.

Any material can be employed as the image-receiving layer in this invention as long as the desired function of mordanting or otherwise fixing the dye images is obtained. The particular material chosen will, of course, depend upon the dye to be mordanted. Suitable materials are disclosed on pages 80 through 82 of the November 1976 edition of *Research Disclosure,* the disclosure of which is hereby incorporated by reference.

Use of a pH-lowering material in the film units employed in this invention will usually increase the stability of the transferred image. Generally, the pH-lowering material will effect a reduction in the pH of the image layer from about 13 or 14 to at least 11 and preferably 5 to 8 within a short time after imbibition. Suitable materials and their functioning are disclosed on pages 22 and 23 of the July 1974 edition of *Research Disclosure* and pages 35 through 37 of the July 1975 edition of *Research Disclosure,* the disclosures of which are hereby incorporated by reference.

A timing or inert spacer layer can be employed in the practice of this invention over the pH-lowering layer which "times" or controls the pH reduction as a function of the rate at which alkali diffuses through the inert spacer layer. Examples of such timing layers and their functioning are disclosed in the *Research Disclosure* articles mentioned in the paragraph above concerning pH-lowering layers.

The alkaline processing composition employed in this invention is the conventional aqueous solution of an alkaline material, e.g., alkali metal hydroxides or carbonates such as sodium hydroxide, sodium carbonate or an amine such as diethylamine, preferably possessing a pH in excess of 11, and preferably containing a developer agent as described previously. Suitable materials and addenda frequently added to such compositions are disclosed on pages 79 and 80 of the November 1976 edition of *Research Disclosure,* the disclosure of which is hereby incorporated by reference.

While the alkaline processing composition used in this invention can be employed in a rupturable container, as described previously, to conveniently facilitate the introduction of processing composition into the film unit, other methods of inserting processing composition into the film unit could also be employed, e.g., interjecting processing solution with communicating members similar to hypodermic syringes which are attached either to a camera or camera cartridge. The processing composition may also be applied by means of a swab or by dipping in a bath, if so desired.

The alkaline solution-permeable, substantially opaque, light-reflective layer employed in certain embodiments of photographic film units used in this invention are described more fully in the November 1976 edition of *Research Disclosure,* page 82, the disclosure of which is hereby incorporated by reference.

The supports for the photographic elements used in this invention can be any material as long as it does not deleteriously affect the photographic properties of the film unit and is dimensionally stable. Typical flexible sheet materials are described on page 85 of the November 1976 edition of *Research Disclosure,* the disclosure of which is hereby incorporated by reference.

While the invention has been described with reference to layers of silver halide emulsions and dye image-providing materials, dotwise coating, such as would be obtained using a gravure printing technique, could also be employed. In this technique, small dots of blue-, green- and red-sensitive emulsions have associated therewith, respectively, dots of yellow, magenta and cyan color-providing substances. After development, the transferred dyes would tend to fuse together into a continuous tone.

The silver halide emulsions useful in this invention, both negative-working and direct-positive ones, are well known to those skilled in the art and are described in *Product Licensing Index,* Volume 92, December 1971, publication 9232, page 107, paragraph I, "Emulsion types"; they may be chemically and spectrally sensitized as described on page 107, paragraph III, "Chemical sensitization", and pages 108 and 109, paragraph XV, "Spectral sensitization", of the above article; they can be protected against the production of fog and can be stabilized against loss of sensitivity during keeping by employing the materials described on page 107, paragraph V, "Antifoggants and stabilizers", of the above article; they can contain development modifiers, hardeners, and coating aids as described on pages 107 and 108, paragraph IV, "Development modifiers"; paragraph VII, "Hardeners"; and paragraph XII, "Coating aids", of the above article; they and other layers in the photographic elements used in this invention can contain plasticizers, vehicles and filter dyes described on page 108, paragraph XI, "Plasticizers and lubricants", and paragraph VIII, "Vehicles", and page 109, paragraph XVI, "Absorbing and filter dyes", of the above article; they and other layers in the photographic elements used in this invention may contain addenda which are incorporated by using the procedures described on page 109, paragraph XVII, "Methods of addition", of the above article; and they can be coated by using the various techniques described on page 109, paragraph XVIII, "Coating procedures", of the above article, the disclosures of which are hereby incorporated by reference.

The term "nondiffusing" used herein has the meaning commonly applied to the term in photography and denotes materials that for all practical purposes do not migrate or wander through organic colloid layers, such as gelatin, in the photographic elements of the invention in an alkaline medium and preferably when processed in a medium having a pH of 11 or greater. The same meaning is to be attached to the term "immobile". The term "diffusible" as applied to the materials of this invention has the converse meaning and denotes materials having the property of diffusing effectively through the colloid layers of the photographic elements in an alkaline medium in the presence of "nondiffusing" materials. "Mobile" has the same meaning.

The term "associated therewith" as used herein is intended to mean that the materials can be in either the same or different layers so long as the materials are accessible to one another.

EXAMPLE 1—Compound 1

The synthesis of the above compound may be described in broad terms as follows:

Ballast-Carrier-$SO_2Cl$ + $H_2N$ - Coup

Ballast-Carrier-$SO_2NH$-Coup

Diazonium salt
$N{\equiv}\overset{+}{N}{-}R$

Ballast-Carrier-$SO_2NH$-Coup-N=N—R wherein Coup is the radical of a coupling component and R is the radical of a diazo component.

In an alternative synthesis, the $SO_2Cl$ moiety could be replaced by a COCl moiety. In another alternative synthesis, the coupler moiety could be protected, for example, by acylation, before being reacted with a linking group, followed by removal of the protecting moiety, e.g., by hydrolysis under acidic conditions, followed by reaction with the diazonium salt followed by reaction with a ballasted carrier. In accordance with the first synthesis as outlined above,

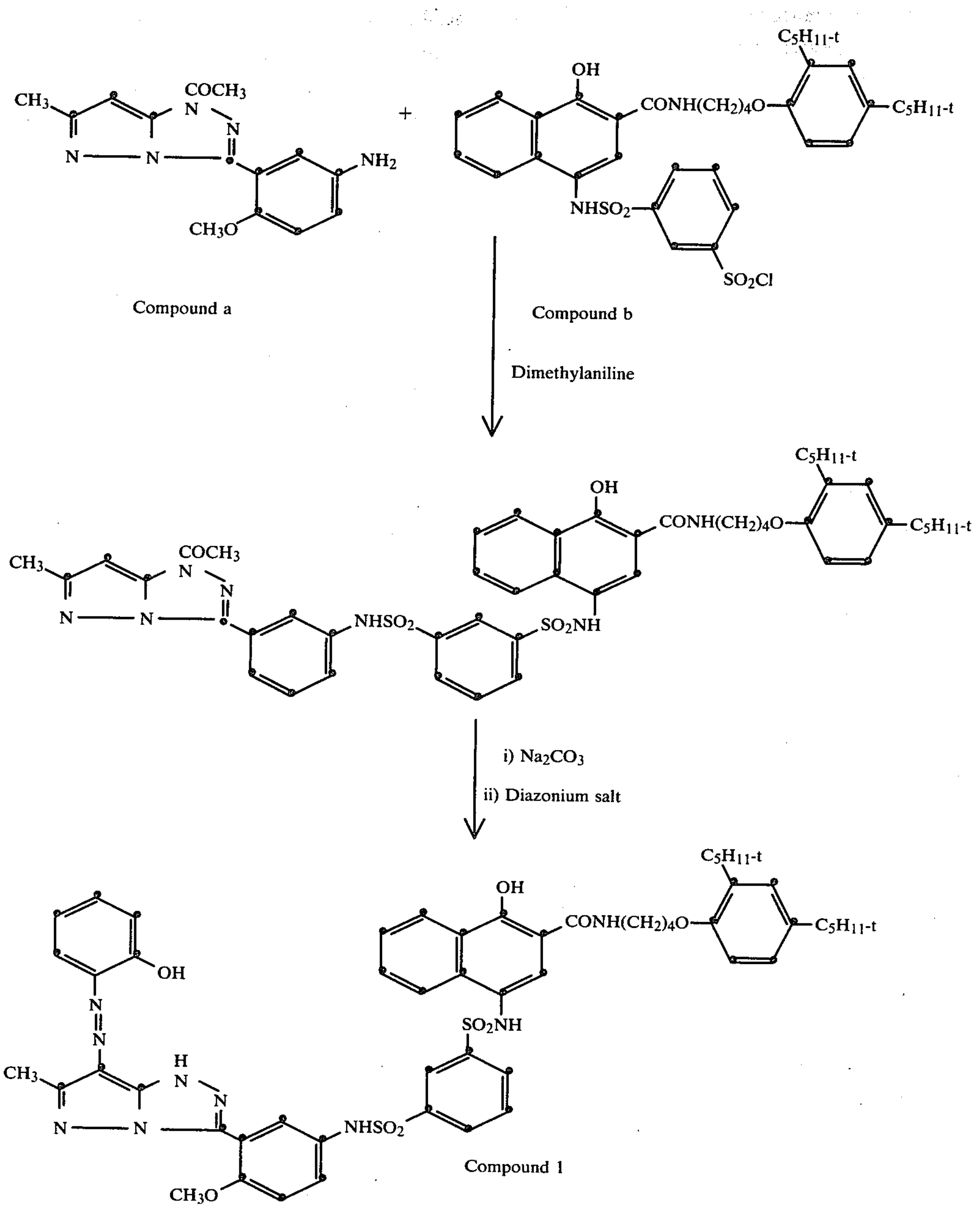

Compound a
Compound b
Compound 1

3-(1-Acetyl-6-methyl-1H-pyrazolo[3,2-c]-s-triazol-3-yl)-4-methoxyaniline (Compound a) (285 mg, 1 m.mol) was dissolved in acetone (25 ml) and dimethylaniline (250 mg) was added. To the reaction mixture was added a solution of 4-(m-chloro-sulphonylbenzenesulphonamido)-1-hydroxy-N-[4-(2,4-di-t-pentylphenoxy)-butyl]naphth-2-amide (Compound b) (720 mg, 1 m.mol) in acetone (25 ml) and the mixture was stirred for 24 hours. The reaction mixture was filtered and the solvent was removed in vacuo. The residual oil, which gave one major spot on thin layer chromatography, was used without purification in the following reaction.

The residual oil (1.0 g≙1 m.mol) was dissolved in ethanol (10 ml) and to this solution was added, with stirring in an atmosphere of nitrogen, a solution of sodium carbonate (1.06 g, 10 m.mol) in water (5 ml). The resultant suspension was stirred for 10 minutes, then cooled in ice. The diazonium salt solution [prepared from 2-aminophenol (0.11 g, 1 m.mol) in ethanol (5 ml) containing five drops of concentrated hydrochloric acid was cooled in ice to 3° C. and treated with a solution of amyl nitrite (0.15 g, 1.3 m.mol) in ethanol (5 ml), keeping the temperature below 5° C.] was added dropwise to the above suspension, under nitrogen, while maintaining the temperature below 10° C. The mixture was allowed to come to room temperature and was then stirred for a further 12 hours under nitrogen.

The red solution was poured into ice water (50 ml) containing concentrated hydrochloric acid (3 ml) and the brown precipitate was filtered off and dried. The crude dye was dissolved in boiling ethyl acetate and petroleum ether (b.p. 60° to 80° C.) was added until the solution was just turbid. On cooling, the resulting dye precipitated as a yellow-brown powder (0.7 g, 66 percent based on the starting pyrazolotriazole) m.p. 150° to 155° C. (slow decomposition). Thin layer chromatography (silica gel, ethyl acetate) gave one spot, Rf=0.6.

$C_{55}H_{61}N_9O_9S_2$—Found: C, 61.9; H, 5.9; N, 10.7; S, 5.7. Calculated: C, 62.6; H, 5.8; N, 11.9; S, 6.1%.

The product was dispersed in gelatin and coated on poly(ethylene terephthalate) film support at the concentration of 0.6 g. product and 1.7 g. gelatin per square meter. This layer was overcoated with a blue-sensitive silver halide emulsion at the concentration of 1.1 g. Ag and 1.1 g. gelatin per square meter. This coating was exposed and processed with a processing composition described below for two minutes in contact with a receiving sheet containing poly(styrene-co-N,N-dimethyl-N-benzyl-N-3-maleimidopropylammonium)chloride as mordant and cupric ions as metallizing agent.

A negative image was formed on the receiving sheet. The image had good density, discrimination was good, but some stain was present in $D_{min}$ areas. The image color was red.

| Processing Composition | | |
|---|---|---|
| Water | 25 | ml |
| Potassium hydroxide | 1.4 | g |
| 5-methylbenzotriazole | 0.06 | g |
| t-butyl hydroquinone | 0.01 | g |
| Anhydrous sodium sulfite | 1.25 | g |
| Aminopropanol | 0.5 | g |
| 4-hydroxymethyl-4-methyl-1-phenyl-3-pyrazolidone | 0.2 | g |
| Hydroxyethyl cellulose | 0.6 | g |

EXAMPLE 2—Compound 11

Preparation of 3-Fluorosulphonyl-N-[3-hydroxy-6-(2-hydroxy-4-nitrophenylazo)pyrid-2-yl]benzamide 2-Amine-6-(2-hydroxy-4-nitrophenylazo)-pyridine-3-ol (4.13 g, 15 mm) was dissolved in dry pyridine (50 ml) and the solution cooled to 0° C. in an ice-salt bath.

3-Fluorosulphonylbenzoyl chloride (3.5 g, 16 mm) in dry tetrahydrofuran (20 ml) was added dropwise to the stirred solution while maintaining the temperature at 0° C. The solution was stirred for 2 hours at this temperature, then allowed to rise to room temperature overnight. The reaction mixture was poured into water (500 ml) containing hydrochloric acid (50 ml) and the resultant precipitate was filtered off, washed with cold water and dried (6.0 g, 87 percent). The crude product was recrystallized from glacial acetic acid to give the pure product as a dark red powder (4.7 g, 68 percent).

$C_{18}H_{12}FN_5O_7S$—Calculated: C, 46.9; H, 2.6; F, 3.8; N, 15.2; S, 6.9. Found: C, 47.2; H, 3.1; F, 4.1; N, 14.6; S, 7.0.

Infrared spectroscopy indicated that the product was the benzamide (C=0, 1670 $cm^{-1}$) with no ester (1750 $cm^{-1}$) present.

Preparation of Compound 11

Sodium carbonate (2.6 g, 25 m.mole) was added to dry dimethyl sulphoxide (25 ml) and the suspension was stirred at 90° C. under dry nitrogen for 30 minutes. 1-Hydroxy-4-amino-N-[4-(2,4-di-t-pentylphenoxy)tetramethylene]naphth-2-amide (1.3 g, 2.8 m.mole) was added in one portion and the mixture stirred for a further 30 minutes at 90° C. 3-Fluorosulphonyl-N-[3-hydroxy-6-(2-hydroxy-4-nitrophenylazo)pyrid-2-yl]benzamide (1.2 g, 2.6 m.mole) was added and stirring was continued. T.L.C. analysis of the reaction mixture indicated that the reaction had gone to completion after 4 hours. The reaction mixture was poured into water (500 ml) acidified with hydrochloric acid (50 ml) and the resultant precipitate was filtered off. The moist solid was taken up in ethyl acetate (50 ml) and the organic solution was washed with water (4×25 ml), then dried over magnesium sulfate. The organic solution was poured into hexane (200 ml) and the precipitated solid was filtered, washed with hexane, then dried under vacuum to give the product (1.9 g, 78 percent).

$C_{49}H_{53}N_7O_{10}S$—Calculated: C, 63.2; H, 5.7; N, 10.5; S, 3.4. Found: C, 63.1; H, 5.9; N, 10.9; S, 3.2%.

EXAMPLE 3—Compound 12

Sodium carbonate (5.3 g, 50 m.mole) was added to dry dimethyl sulphoxide (50 ml) and the suspension was stirred at 90° C. under dry nitrogen for 30 minutes. 1-Hydroxy-4-amino-N,N-(didodecyl)naphth-2-amide (2.69 g, 5 m.mole) was added in one portion and the mixture was stirred for a further 30 minutes. 3-Fluorosulphonyl-N-[3-hydroxy-6-(2-hydroxy-4-nitrophenylazo)pyrid-2-yl]benzamide (2.30 g, 5 m.mole) was added in one portion and the solution was stirred for 90 minutes at 90° C. The cooled solution was poured into water (1 liter) containing hydrochloric acid, thus giving a thick brown-black precipitate which was filtered off and washed with water. The crude, waxy solid was digested with hot ethyl acetate (3×100 ml); the residue was discarded, and the organic extracts were combined, washed with water and dried over magnesium sulfate. The solvent was evaporated to give a dark oily glass which was taken up in hot acetic acid and then poured slowly into ice water (1 liter) with vigorous stirring. The flocculant precipitate was allowed to stand overnight in the cold store, then filtered off, washed copiously with water until the washings were at neutral pH and then air dried. The product was obtained as a brown friable solid (3.0 g, 60 percent).

$C_{53}H_{69}N_7O_9S$—Calculated: C, 65.0; H, 7.0; N, 10.0. Found: C, 65.2; H, 7.4; N, 9.4%.

The product was dispersed in a silver halide emulsion and coated on poly(ethylene terephthalate) film support at the concentration of 80 mg silver/$ft^2$, $5\times10^{-5}$ moles of product/$ft^2$ and 150 mg/gelatin/$ft^2$. This layer was overcoated with gelatin at 82.5 mg/$ft^2$. This coating was exposed and processed with a processing composition described below for two minutes in contact with a receiving sheet containing poly(styrene-co-N,N-dimethyl-N-benzyl-N-3-maleimidopropylammonium)-chloride as mordant. The receiving sheet was washed, then dipped in an afterbath containing ammonium copper sulfate.

A negative image was formed on the receiving sheet. The image had good density and good discrimination, but some stain was present in $D_{min}$ areas. The image color was cyan, and the dye was found to be very stable to heat and light.

| Processing Composition | | |
|---|---|---|
| Solid sodium hydroxide | 0.5 | g |
| 1 N sodium hydroxide solution | 25 | ml |
| 5-methylbenzotriazole | 0.005 | g |
| t-butyl hydroquinone | 0.005 | g |
| Potassium bromide | 0.125 | g |
| 4-hydroxymethyl-4-methyl-1-phenyl-3-pyrazolidone | 0.125 | g |

-continued

| Processing Composition | | |
|---|---|---|
| hydroxyethyl cellulose | 0.35 | g |

The invention has been described in detail with particular reference to preferred embodiments thereof, but it will be understood that variations and modifications can be effected within the spirit and scope of the invention.

What is claimed is:

1. A coordination complex of a polyvalent metal ion and a compound having the following formula:

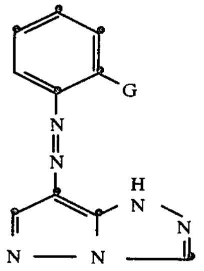

wherein:

G is a metal chelating group.

2. The complex of claim 1 wherein the metal ion is nickel (II), copper (II), zinc (II), platinum (II), palladium (II), or cobalt (II).

3. The complex of claim 1 wherein G is hydroxy.

4. A coordination complex of a polyvalent metal ion and a compound having the following formula:

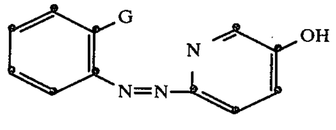

wherein:

G is a metal chelating group.

5. The complex of claim 4 wherein the metal ion is nickel (II), copper (II), zinc (II), platinum (II), palladium (II), or cobalt (II).

6. The complex of claim 4 wherein G is hydroxy.

7. The complex of claim 4 wherein the phenyl group is substituted with a nitro group para to the azo linkage and the pyridine ring is substituted with an amino group.

8. A photographic element comprising a support having thereon a layer comprising a photographic mordant and bound thereto a coordination complex of a polyvalent metal ion and a compound having the following formula:

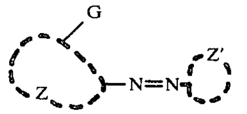

wherein:

Z represents the atoms necessary to complete an aromatic carbocyclic or heterocyclic nucleus having at least one ring of 5 to 7 atoms;

Z' is an aromatic carbocyclic or heterocyclic nucleus having at least one ring of 5 to 7 atoms, said Z' having, in a position adjacent to the point of attachment to the azo linkage, either (a) a nitrogen atom in said ring of said nucleus which acts as a chelating site, or (b) a carbon atom in said ring of said nucleus having directly attached thereto a nitrogen atom which acts as a chelating site; and G is a metal chelating group.

9. The photographic element of claim 8 wherein Z represents the atoms necessary to complete a phenyl group and Z' represents a pyrazolotriazole nucleus.

10. The photographic element of claim 8 wherein Z represents the atoms necessary to complete a phenyl group and Z' represents a pyridinol nucleus.

11. The photographic element of claim 8 wherein the metal ion is nickel (II), copper (II), zinc (II), platinum (II), palladium (II), or cobalt (II).

12. The photographic element of claim 8 wherein G is hydroxy.

13. The photographic element of claim 8 wherein said compound has the formula:

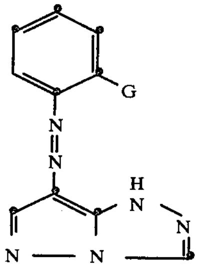

wherein:

G is a metal chelating group.

14. The photographic element of claim 13 wherein the metal ion is nickel (II), copper (II), zinc (II), platinum (II), palladium (II), or cobalt (II).

15. The photographic element of claim 13 wherein G is hydroxy.

16. The photographic element of claim 8 wherein said compound has the formula:

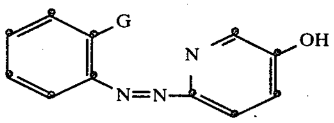

wherein:

G is a metal chelating group.

17. The photographic element of claim 16 wherein the metal ion is nickel (II), copper (II), zinc (II), platinum (II), palladium (II), or cobalt (II).

18. The photographic element of claim 16 wherein G is hydroxy.

19. The photographic element of claim 16 wherein the phenyl group is substituted with a nitro group para to the azo linkage and the pyridine ring is substituted in the 2-position with an amino group.

* * * * *